United States Patent [19]

Tuckett et al.

[11] Patent Number: 5,381,805

[45] Date of Patent: Jan. 17, 1995

[54] CUTANEOUS TESTING DEVICE FOR DETERMINING NERVOUS SYSTEM FUNCTION

[75] Inventors: Robert P. Tuckett; Kenneth W. Horch; John H. Fisher, all of Salt Lake City; Barry L. Evans, Murray, all of Utah

[73] Assignee: Topical Testing, Inc., Salt Lake City, Utah

[21] Appl. No.: 943,438

[22] Filed: Sep. 9, 1992

Related U.S. Application Data

[63] Continuation-in-part of Ser. No. 713,397, Jun. 10, 1991, which is a continuation-in-part of Ser. No. 469,280, Jan. 24, 1990, Pat. No. 5,022,407.

[51] Int. Cl.[6] ............................................. A61B 5/00
[52] U.S. Cl. ..................................... 128/739; 128/741; 128/742; 128/744
[58] Field of Search ................ 128/734, 739, 741–742, 128/744, 774, 782

[56] References Cited

U.S. PATENT DOCUMENTS

| | | | |
|---|---|---|---|
| 3,703,101 | 11/1972 | Pence | 128/782 X |
| 3,886,931 | 6/1975 | Rodler | 128/741 |
| 4,064,870 | 12/1977 | Dumitrescu et al. | 128/741 |
| 4,277,828 | 7/1981 | Tateishi | 364/415 |
| 4,299,230 | 11/1981 | Kubota | 128/630 |
| 4,306,291 | 12/1981 | Zilm et al. | 364/508 |
| 4,356,826 | 11/1982 | Kubota | 128/630 |
| 4,467,815 | 8/1984 | O'Brien et al. | 128/740 |
| 4,503,863 | 3/1985 | Katims | 128/741 |
| 4,641,661 | 2/1987 | Kalarickal | 128/744 |
| 4,653,507 | 3/1987 | Laudadio | 128/742 |
| 4,754,763 | 7/1988 | Doemland | 128/739 |
| 4,763,666 | 8/1988 | Strian et al. | 128/742 |
| 4,794,934 | 1/1989 | Motoyama et al. | 128/734 |
| 4,852,570 | 8/1989 | Levine | 128/630 |
| 4,940,060 | 7/1990 | Gu et al. | 128/735 |
| 5,002,065 | 3/1991 | Lacourse et al. | 128/739 |
| 5,022,407 | 6/1991 | Horch et al. | 128/739 |
| 5,230,345 | 7/1993 | Curran et al. | 128/739 |

FOREIGN PATENT DOCUMENTS

87038306/06 2/1987 France .

OTHER PUBLICATIONS

Grant, et al. "Use of Motor Nerve Conduction Testing and Vibration Sensitivity Testing as Screening Tools for Carpal Tunnel Syndrome in Industry", The Journal of Hand Surgery Jan. 17:71–76 (1992).
Borg, K., et al. "Increase of Vibration Threshold during Wrist Flexion in Patents with Carpal Tunnel Syndrome", Pain 26:211–219 (1986).
Dyck, P., et al. "Introduction of Automated Systems to Evaluate Touch-Pressure, Vibration, and Thermal Cutaneous Sensation in Man", Annals of Neurology, Dec. 4:502–508 (1978).
Dyck, P., et al. "Clinical vs Quantitive Evaluation of Cutaneous Sensation", Arch Neurol Sep. 33:651–655 (1978).
Dyck, P., et al. "Description of Minnesota Thermal Disks and normal values of cutaneous thermal discrimination in man", Neurology Apr. 325–330 (1974).
Dyck, P., Schultz, P. "Quantitation of Touch-Pressure Sensation", Arch Neurol May 26:465–473 (1972).
Chubbuck, J. "Small Motion Biological Stimulator", APL Technical Digest 18–23 (May–Jun. 1966).

Primary Examiner—Angela D. Sykes
Attorney, Agent, or Firm—Madson & Metcalf

[57] ABSTRACT

An automatic apparatus for testing cutaneous responses of a patient is disclosed. The embodiments of the invention variously include components for: applying a nonambient temperature to the patient's skin to test the patient's response to thermal stimuli; pricking the patient's skin to test the patient's response to pain; indenting the patient's skin to test the patient's response to touch; vibrating the patient's skin to test the patient's response to vibration; and for making two spaced apart contacts with the patient's skin to test the patient's two point discrimination response. A general purpose computer and dedicated control circuits function to control the operation of the system and record the responses of the patient. The embodiments of the present invention are able to repeatedly reproduce each test so that the tests carried out are reproducible and accomplished in a minimum of time.

22 Claims, 4 Drawing Sheets

CUTANEOUS TESTING DEVICE FOR DETERMINING NERVOUS SYSTEM FUNCTION

RELATED APPLICATIONS

This application is a continuation-in-part of applicants' copending application Ser. No. 07/713,397, filed Jun. 10, 1991, now allowed, entitled "Tactile Testing Device and Methods," which is a continuation-in-part of Ser. No. 07/469,280, filed Jan. 24, 1990, now U.S. Pat. No. 5,022,407, issued Jun. 11, 1991, and entitled "Apparatus For Automated Tactile Testing," both of which are incorporated herein by this reference.

BACKGROUND

1. The Field of the Invention

This invention relates to apparatus used to determine the response of a patient to cutaneous stimulation. More particularly, the present invention relates to systems and methods for quantifiably determining a patient's responses to a variety of cutaneous stimuli in a repeatable and reproducible manner.

2. Technical Background

Many medical professionals and researchers have need to determine a patient's response to various modes of cutaneous stimulus. For example, medical professionals dealing with the human nervous system often need to determine a patient's response to various cutaneous stimuli to assess the extent of any damage to the nervous system due to trauma or a degenerative condition.

Still further, rehabilitation and physical therapists concerned with monitoring a patient's progress during recovery from a head injury, stroke, or some other event affecting somatosensory function also must conduct cutaneous or tactile testing. Moreover, primary care providers often desire to perform cutaneous testing as a routine screening procedure for their patients but have been unable to do so because of the specialized training, equipment, and experience needed to perform such testing using existing methods.

One area of particular interest and concern is the assessment and diagnosis of nerve damage affecting the function of the hand. Damage to the nerves serving the hand gives rise to a number of potential problems. In particular, there is a high level of concern over the increased incidence of carpal tunnel syndrome. Carpal tunnel syndrome gives rise to numbness, tingling, and pain, which often occurs when the person is away from the causative activity. This lack of relationship between the symptoms of carpal tunnel syndrome and the offending activity often leads to delay in identifying the problem and in seeking appropriate treatment. This delay may lead to increased injury and even permanent disability.

Within the last decade the incidence of carpal tunnel syndrome and related traumatic injuries have risen dramatically. The United States Bureau of Labor Statistics indicates that cumulative trauma disorders of this type were responsible for approximately 53% of the occupational illness reported by the private sector in 1989. Of these, carpal tunnel syndrome ranked second only to back injuries as the most frequently reported and most costly of Worker's Compensation claims.

Early detection of the problem can often prevent further damage and stop the progression of the trauma. It is apparent, therefore, that there is an increasing need for diagnosis and detection of carpal tunnel syndrome and similar disorders. Yet accurate and early detection has been difficult with known techniques and equipment.

Despite the clear need for repeatable, quantitative testing methods, evaluation of cutaneous function is normally done using manual testing techniques. Typically, the clinician stimulates the skin of the patient with one or more handheld testing devices, such as needles, tuning forks, hairs, filaments of varying stiffness, or dividers with varying separation between points. The patient then reports on the sensation achieved.

Manual procedures have a number of commonly recognized drawbacks. The clinician and, to some extent the patient, control the stimulus sequence, the interval between stimuli, the stimulus amplitude, and so on. The subject can obtain real or imagined cues from the clinician during the tests, and then second-guess in an attempt to improve or worsen his performance. All of these factors, which can have a significant effect on the outcome of the tests, may vary from session to session, limiting the validity of the resulting data. Moreover, other tests, such as those that measure vibrotactile threshold at different frequencies, temperature perception, and level of shape-dull awareness, are of diagnostic value, but cannot be readily and reproducible performed manually.

In designing testing procedures and equipment it must be remembered that normal cutaneous sensation is the result of central interpretation of sensory input from a mixture of receptor types in the skin. These sensations are mediated by a number of specialized and modality-specific nerve fibers. For example, touch and vibration sense in glabrous skin is subserved by at least four different types of myelinated nerve fibers. Temperature is subserved by two classes of fibers and pain by both the small myelinated and unmyelinated nerve fibers. It would, therefore, be ideal to have the capability of measuring independently, the performance of the three major modes of sensation It is generally necessary to test all three of the principal modalities of cutaneous sensation, i.e., temperature, pain, and touch, in order to completely assess a patient's condition. As mentioned above, existing methods of testing the patient's thresholds and suprathresholds of temperature, pain, and touch involve manually applying the stimulus to the patient. Such manual methods are time consuming to prepare and administer, require a subjective determination by the administering technician, and are not consistently applied or reproducible from test to test.

In view of the foregoing, it would be an advancement in the art to provide apparatus and methods for accurately and reproducibility testing a patient's responses to one or more cutaneous stimuli. It would also be an advancement in the art to provide apparatus and methods for automatically testing a patient's response to various modes of cutaneous stimulation which does not require special expertise to operate and maintains a record of the results of the testing. It would be a further advancement in the art to provide a system and methods for automatically testing the cutaneous responses of a patient which imposes quantifiably accurate stimuli upon command and which carries out the testing in a relatively short period of time.

It would be of particular interest to provide a system which was able to control the amplitude, velocity, and time course of stimulation. It would be a further advancement to provide such a system which was designed to measure human cutaneous sensory threshold in a quick and efficient manner, thus being capable of rapidly screening subjects for early signs of sensory deficit. It would also be an advancement in the art to provide such a system which was designed such that neither the operator nor the subject was aware of the timing of the stimulus delivery. Finally, it would be a significant advancement to provide computer means for receiving data and for controlling the set of stimuli administered in order to obtain a predetermined data set.

Such methods and apparatus are disclosed and claimed herein.

BRIEF SUMMARY AND OBJECTS OF THE INVENTION

The present invention provides cutaneous testing apparatus and methods. The apparatus preferably provides means for cutaneous stimulation of a patient. Various stimuli, such as elevated or reduced amplitude of temperature, vibration, indentation, pinprick force, amplitude of two point discrimination, electrical current, and other similar types of cutaneous stimuli, may be administered in order to stimulate selected nerves and nerve fibers and in order to test the functions of those nerves and fibers.

The device is also provided with control means for accurately controlling the amplitude of stimulus administered by operation of the stimulation means, such that stimuli of precise predetermined amplitude are administered. As will be discussed below, these functions are accomplished by the use of mechanical and electrical controls in communication with a computer. The computer provides a number of control and data recording functions, including means for recording patient response to the stimuli. Responses to the stimuli may be recorded either voluntarily by the patient, or by the measurement of physical or physiological changes in the patient. Finally, the apparatus is provided with computer means for generating additional stimuli in response to the record of the patient response such that a set of data can be collected.

The present invention also includes unique means for positioning the portion of the patient's anatomy being tested. For example, the patient's hand may be comfortably and accurately positioned in order to allow testing to proceed. This facilitates the collection of data, and assures that accurate and reproducible testing occurs. The rounded shape of the stimulator surface allows the hand to rest on the stimulator in a relaxed, natural manner which minimizes the stress placed on the carpal tunnel area.

The present invention is capable of automatically testing the three principal modalities of cutaneous sensation: temperature, pain, and touch. The control means of the present invention provides for precise control of stimulus waveforms (temperature, force, indentation as a function of time, or current) so that reliable, quantitative data is obtained from the testing. The embodiments of the present invention are able to reproduce each test waveform from a consistent initial condition and use predetermined sequences of stimuli so that the tests carried out are reproducible and accomplished in a minimum of time.

The method of operating the computer included in the control means minimizes the need for technical expertise on the part of the operating technicians. The method of operating the computer also maximizes the present invention's flexibility by allowing new stimulus paradigms to be incorporated into the testing protocol by altering the programming code of the control means. This feature allows the embodiments of the present invention to modify the operation of the system in response to user requests or advances in the methodology of somatosensory testing by merely altering the programming code.

In addition, the present invention can be operated in such a manner that operator involvement is minimized. As mentioned above, the present invention can be provided with means for allowing the patient to directly input responses to stimulation. For example, the patient may depress a button when he first feels a stimulation. In another embodiment, the patient may position a slide to indicate the perceived intensity of the stimulus. Alternatively, the patient may be equipped with a monitor that measures nerve conduction velocity or other physiological response to the stimulus. The system records the input of the patient, and may produce subsequent stimuli in response to the recorded response.

In this regard, the apparatus may be operated in such a manner that neither the operator, nor the patient has any advance clue concerning the amplitude, timing, or duration of the test stimulus administered. The test is administered automatically as a function of the computer software and the patient's responses to previous stimuli.

The device is also readily usable in tests employing provocative stimulation. For example, placing pressure on the median nerve in the carpal tunnel area, or obstructing blood flow will increase the carpal tunnel symptoms. Thus, carpal tunnel dysfunction can be detected early. Alternatively, the hand and wrist may be positioned so as to intentionally irritate a suspected condition.

The present invention also provides a novel testing module for housing the various stimulation mechanisms, and for providing a convenient and reproducible placement of the portion of the patient being tested. In one embodiment of the invention, the testing module is equipped with a hemispherical dome configured such that the testing apparatus can substantially reside under the dome. Testing apparatus which may be placed under the dome include, but is not limited to, a vibrating probe, thermal probe, constant force probe, and two-point discrimination probe. One or more openings are provided in the dome such that the testing apparatus can selectively extend out of the dome and contact the patient.

The dome is easily rotatable in order to allow for testing by various probes at various places on the hand, or other part of the patient. The testing module may be provided with indicia which indicate the position of the dome. Typically indicia will be provided on the testing module, with corresponding indicia on the dome. In this manner, the exact position of the dome is known and can be accurately reproduced in subsequent tests.

The testing module dome is particularly ergonomic in design. The hand can easily and comfortably rest over the dome. In one embodiment of the invention, the testing module is also equipped with an arm rest. This feature makes the testing procedure more comfortable. By adjusting the arm rest, it is also possible to compress specified nerves, muscles, or skin areas in order to perform specific provocative testing.

Using the arm rest, it is possible to obtain more accurate and reproducible data in that the position of the hand and arm are controlled. In one embodiment of the present invention, the arm rest is provided with means for adjustment and two sets of indicia which allow the arm rest to be positioned at an exact location. The indicia may allow for positioning of the arm rest in a vertical and horizontal rotational plane.

In this manner it is possible, for example, to test compression injuries of the nerves innervating the hand. The device can not only test the functionality of median nerve which passes through the carpal tunnel, and which innervates primarily the index and middle fingers, but also the ulnar nerve which innervates the little finger, and the radial nerve which innervates the thumb. The apparatus allows for testing for carpal tunnel syndrome, as well as injuries and diseases at other locations, such as the spinal cord.

Reproducible data is collected in that the patient is unable to anticipate the stimulus, and subjective factors in administering the stimulus are eliminated. The device may be programmed such that stimuli or selected amplitude are administered at intervals which cannot easily be anticipated by the patient or the operator. For example, the device may be programmed to perform a "search" routine, where the magnitude of the stimulus is varied quickly until the patient's approximate threshold is located. The device may then undertake a "staircase" routine in which a more detailed set of tests within a more narrow range of stimulus amplitude are generated in order to determine the exact level of the patient's ability to respond.

The present invention can perform diagnostic clinical tests for which manual methods are inadequate, such as determining threshold values for sensing changes in vibratory frequency. The present invention also has application in research settings where testing to determine responses to cutaneous stimuli are important, such as in the study of peripheral nerve regeneration.

Because the present invention utilizes automated testing sequences and stimulus presentations, it takes less time to collect data for each patient. Furthermore, subjective problems such as observer bias and interactions between subject and technician are reduced or eliminated, particularly where the patient directly inputs signals in response to stimuli.

Since the present invention may be operated by a technician with only little experience with the system, the surgeon or other medical practitioner is freed from performing a task that may become routine. It is only necessary that a standardized procedure be carried out by a technician. This ease of use of the system facilitates periodic retesting of patients, retesting being a prerequisite for properly evaluating the course of disease or a patient's recovery after undergoing a procedure.

In view of the foregoing, the present invention seeks to realize the following objects and advantages.

It is an object of the present invention to provide apparatus and methods for accurately and reproducibility testing a patient's responses to one or more cutaneous stimuli.

It is a further object of the present invention to provide apparatus and methods for automatically testing a patient's response to various modes of cutaneous stimulation which does not require special expertise to operate and maintains a record of the results of the testing.

It is also an object of the present invention to provide apparatus and methods for automatically testing the cutaneous responses of a patient which imposes quantifiably accurate stimuli upon command and which carries out the testing in a relatively short period of time.

It is another object of the present invention to provide a system which is able to control the amplitude, velocity, and time course of stimulation applied.

It is a related object of the present invention to provide such a system which is designed to measure human cutaneous sensory threshold in a quick and efficient manner, thus being capable of rapidly screening subjects for early signs of sensory deficit.

It is also an object of the present invention to provide such a system which is designed such that neither the operator nor the subject is aware of the timing of the stimulus delivery.

It is an object of the present invention to use automated and quantifiable provocative tests to enhance preexisting carpal tunnel symptoms and thus enhance early signs of compression injury.

Finally, it is an object of the present invention to provide computer means for controlling the set of stimuli administered, receiving data, and correcting for error factors such as the patient's age in order to obtain a predetermined, clinically relevant data set.

These and other objects of the present invention will become more fully apparent during an examination of this disclosure and the appended claims and by practicing the invention.

DETAILED DESCRIPTION OF THE PREFERRED EMBODIMENT

1. System Overview

Figure 1:
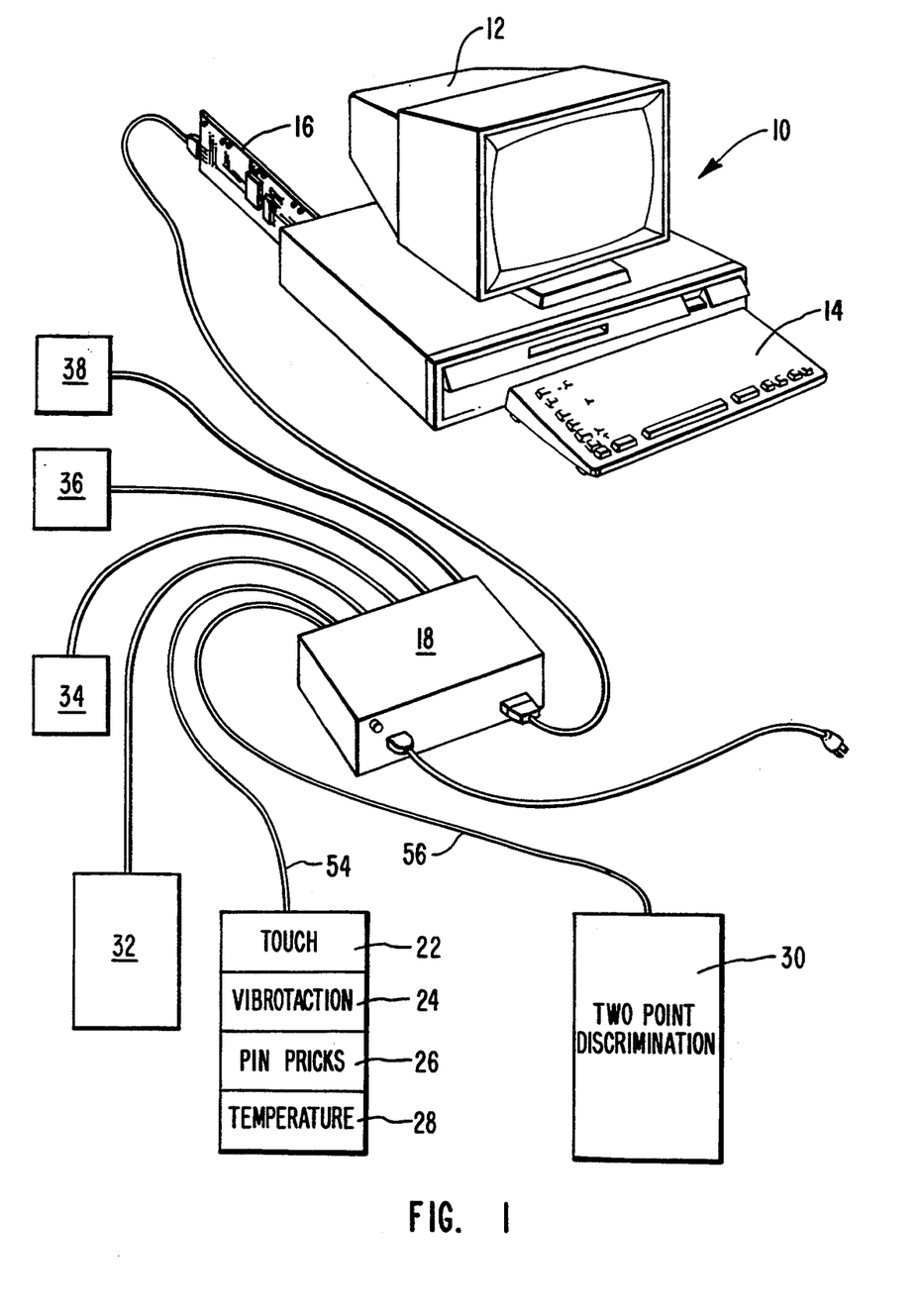
FIG. 1 is an overall view of one embodiment of the present invention.

Reference will now be made to the drawings wherein like structures will be provided with like reference designations. Referring first to FIG. 1, an overall view of one preferred embodiment of the system of the present invention is provided. Represented in FIG. 1 is a microcomputer, generally designated at 10. The computer includes attached monitor 12 and keyboard 14 Also represented in FIG. 1 is a data acquisition board 16, which provides at least six 12-bit digital-to-analog (D/A) converters, eight 12-bit analog-to-digital converters, a timer, and a parallel input-output port to interface between the computer 10 and the dedicated electrical circuits of the control module 18.

The control module 18 represented in FIG. 1 contains the dedicated electrical circuitry necessary to drive and control the various testing apparatus represented at 22, 24, 26, 28, 30, and 32. As illustrated in FIG. 1, testing apparatus 22 comprises means for testing sensitivity to indentation or touch, testing apparatus 24 comprises means for testing sensitivity to vibration (vibrotaction), testing apparatus 26 comprises means for administering pin pricks, testing apparatus 28 provides means for testing sensitivity to cold and heat. Testing apparatus 30 is separately designated and may specifically include means for discriminating between two points. Finally, testing apparatus 32 may, for example, provide means for administering a constant current. As will be discussed in further detail below, all of these testing apparatus may be incorporated into a single testing module.

FIG. 1 also illustrates two monitors 34 and 36. These monitors may be provided with automatic means for the input of data from the patient. The monitors either measure directly patient response, or allow the patient to input a response directly into the system. These monitors will be discussed further below. FIG. 1 also illustrates a pressure cuff 38 attached to the control module 18. This provides the system with the capability of automatically administering a predetermined pressure during stimulus in order to run certain types of provocative testing.

Figure 2:
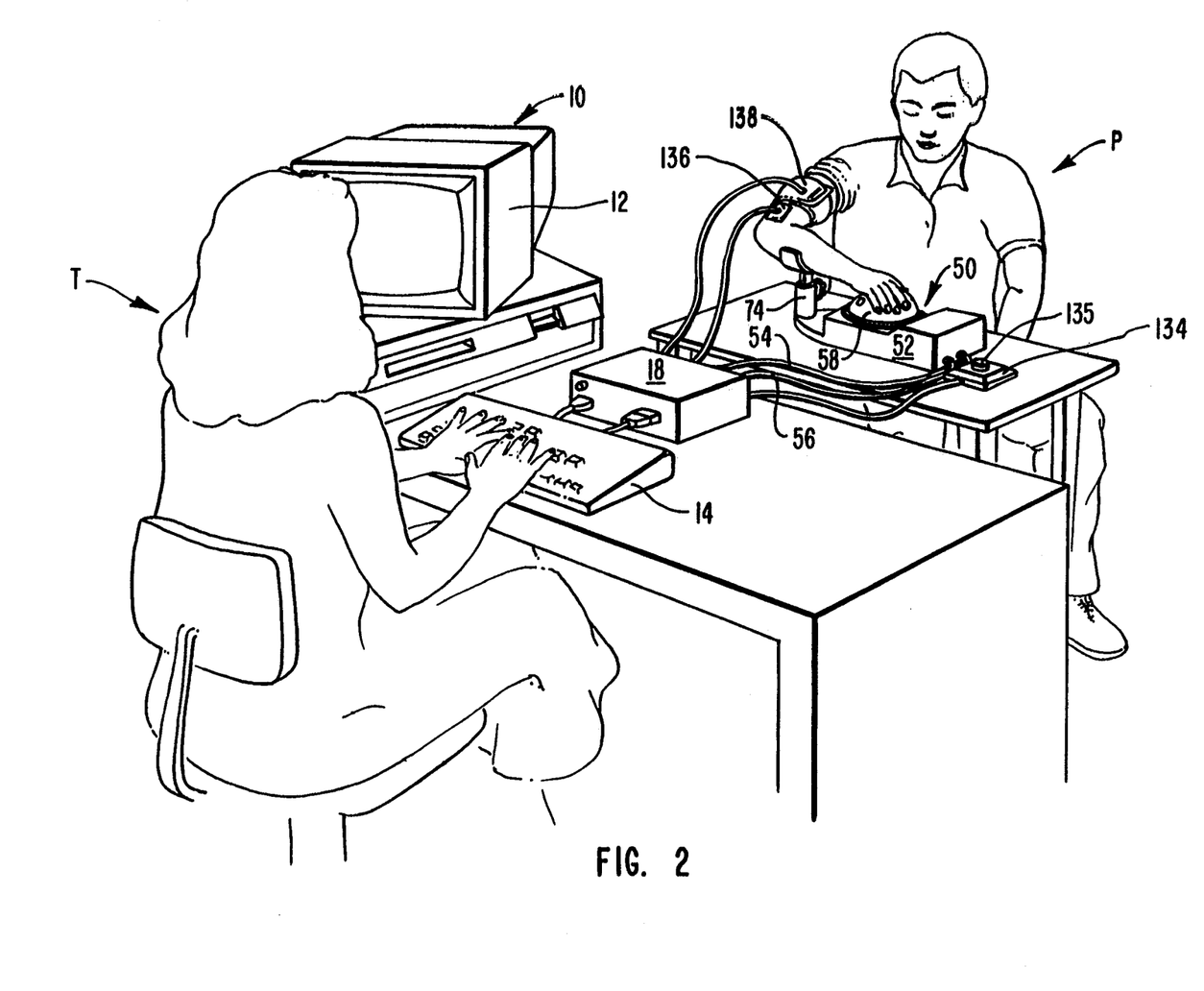
FIG. 2 illustrates one embodiment of the system of the present invention being used to test the cutaneous responses of a patient.

FIG. 2 provides an overall view of the system of the present invention in use. Represented in FIG. 2 is the microcomputer 10, control module 18 and the testing module 50 being operated by a technician T to test the cutaneous response of a patient or subject P. Also illustrated in FIG. 2 are the pressure cuff 138 (which corresponds to pressure cuff 38 in FIG. 1), and two monitors 134 and 136 (which correspond generally to monitors 34 and 36 in FIG. 1). Monitor 134 is positioned such that the patient can input responses by means of a button or slide 135. In one embodiment of the invention, the button 135 is depressed by the patient P during the time that a sensory stimulus is felt. As the stimulus is applied, the patient depresses and then releases the button 135 as soon as the stimulus is felt. Feedback is provided to the system concerning the amplitude and range over which the stimulus is felt by the patient. This data can then be analyzed by means of the computer 10 and compared to the stimulus applied.

Alternatively, monitor 136 may be positioned directly on the patient in order to directly monitor physiological or electrical changes in the patient. The stimulus is administered by the testing module in the manner described herein. The direct electrical or physiological response to the stimulus is then recorded by monitor 136. One type of monitor 136 is a recording electrode manufactured by Harvard, Inc.

The monitors 134 and 136, and button 135 can be used to significantly automate the system. Since the response of the patient can be recorded directly by the system, it is possible to administer a series of tests and record the responses of the patient without constant input from a technician. For example, it will be possible for a physician to teach the patient how to depress the button 135 when a stimulus is felt. Then the system can be programmed to cycle through the desired series of tests as will be discussed in further detail below. Since the patient's responses are automatically recorded by the system, the physician is provided with a full set of data, while minimizing the expense of technician or physician time.

In an alternative embodiment, the monitor 134 may comprise an LED display and a corresponding slide mechanism. The patient moves the slide mechanism along the display in proportion to the perceived stimulus. Again, the patient response (i.e. positioning of the slide) is recorded and correlated with the corresponding stimulus. Thus, direct patient input into the system is provided.

Thus, it can be seen that numerous mechanism exists for direct patient interaction and for directly recording patient responses. The use of these mechanisms reduce the need for technician and physician interaction. They also provide for increased accuracy by the elimination of transcription errors and error in oral communication from the patient to the technician.

2. Testing Apparatus

As mentioned above, the system of the present invention will include one or more mechanisms for administering a cutaneous stimulus to a patient. The stimuli administered may be of various types in order to provide for obtaining specific types of data. Multiple types of stimuli provide means for simulating multiple types of nerve fibers. As mentioned above, different myelinated and unmyelinated nerve fibers are involved in different types of sensory perception.

The operation and structure of representative testing apparatus of each type is discussed in U.S. Pat. No. 5,022,407 to Horch et al., which has been incorporated herein by reference. In addition, other specific means for producing stimuli of the types discussed herein are known to those of skill in the art.

One of the types of testing apparatus discussed includes thermal stimulation means. Thermal stimulation means 28 may include means for providing hot and/or cold stimuli. In one embodiment of the present invention a Peltier cell is used in order to selectively administer either hot or cold stimuli. Alternatively, the thermal stimulation means may comprise a resistive heating element with an embedded thermistor sensor.

For thermal sensory tests, in the presently preferred embodiments, the maximum command temperature is 44.0° C. and the temperature of the stimulation is increased at a rate of 4.5° C./second. A proportional feedback controller is included in the control module which prevents overshoot during step changes in command temperature, and the non-linear (logarithmic) properties of the thermistor are compensated for in the operating code when calculating the proper digital to analog output voltage for a desired temperature.

The maximum available power directed to the resistance coil is 10 watts in the described embodiment, providing a measure of safety in the event of component failure. In some embodiments of the present invention the upper and lower limits on the temperature imposed during thermal stimulation can be increased to provide for testing of nociception with thermal stimuli; temperatures up to 48° C. and down to 5° C. are used to activate thermal pain signaling nerve fibers.

Also shown in FIG. 1 is testing apparatus for administering pin pricks 26. Various mechanism are available. In one embodiment of the device the testing apparatus 26 comprised a pinprick stimulation means comprising a constant torque motor with a return spring. One such constant torque motor is available from Litton Systems, Inc. and described as a TD-1500-c-1 toroidal motor. This mechanism provides for the administration of pin pricks to the patient. Generally, the pin prick apparatus may include a sterile hypodermic needle.

During operation of the components which carry out the pinprick stimulation, a command signal sets the voltage applied to the constant torque motor, which in turn determines the torque (i.e., indentation force) produced by the constant torque motor. The maximum indentation force the system described herein can produce is 0.49 N (50 g-force), and its range of travel is restricted to 3 mm.

A further testing apparatus comprises a vibrotaction stimulation means 24. In one embodiment of the device, the vibrotaction means comprises a galvanometer which moves a hex shaped rod to indent the skin of the patient. The skin is then vibrated until a response is felt by the patient. Mechanical indentation to test touch and vibrotaction responses of the patient is produced by activating a galvanometer. The touch test is an accurate and quantifiable substitute for the monofilament or Von Feyt test for cutaneous sensibility which has been found to be the most discriminitive assay of carpal tunnel symptoms. One such galvanometer is available from General Scanning Inc. and referred to as model GVM620.

In order to provide for precise control of small amplitude stimuli, the driving amplifier for the galvanometer may be equipped with a variable gain which is controlled by the computer. By selecting the proper gain based on the size of the indentation desired, the range digital-to-analog converter is increased by two orders of magnitude. Moreover, the use of galvanometer allows the frequency of the vibration stimuli imposed on the patient's skin to be accurately controlled over a range of one or more hundred Hertz.

Various alternative embodiments are available for providing touch and vibrotaction stimuli. In particular, alternative devices could be mounted within the stimulus module. One such device is the Model GWV4 shaker manufactured by Gearing and Watson Electronic Group, Ltd. This device is capable of operating in the range of DC (0 Hz) to 12 kHz and has a relatively large displacement, on the order of 0.20 inch. This particular device is capable of producing all of the required waveforms for touch and vibrotaction measurements.

A further testing apparatus 30 carries out the two point discrimination stimulus. The two point discrimination apparatus may include a servo motor and a galvanometer. The galvanometer may be obtained from General Scanning Inc. model GVM620. The servo motor may comprises one available from Futaba Denshi Kogyo Kabushiki Kaisha, Chiba-Ken, Japan and designated as a FP-S28 servo.

Using the present invention, testing apparatus 30 imposes two variably spaced points upon the skin of the patient, is able to vary the pressure imposed upon the patient, and modulates (vibrates) the pressure imposed. Thus, it will be appreciated that the components contained within the two point discrimination testing apparatus 30 are able to impose two point discrimination stimulation while also varying the force applied to the patient's skin. Moreover, the galvanometer allows vibrotaction stimulation to be imposed upon the patient combined with the two point discrimination stimulus.

An additional constant current testing apparatus is illustrated at 32 in FIG. 1. With such an apparatus it is possible to electrically activate the patient's nerve fibers and to obtain further measurements concerning nerve function. In order to acquire accurate data concerning nerve function it may be desirable to include a further monitor 36 (which corresponds to monitor 136 in FIG. 2) which is attached directly to the patient. The monitor 36 may, for example, comprise a device for measuring electrical potentials carried by the patient's nerves. In the alternative, monitor 36 may comprise other types of physiological monitors.

In operation, a constant current stimulus can be applied by testing apparatus 32. The result of that stimulus is then measured directly by means of the monitor 36.

Some of the measurements which are possible by this mechanism include conduction velocity through the subject nerves, threshold current levels, types of sensations evoked, magnitude of sensation versus magnitude of stimulus (i.e. does-response), and delay time from stimulus until sensation or an electroencephalographic (EEG) evoked potential.

In typical operation, the constant current generator which forms a part of testing apparatus 32 is isolated from the ground. Two probes extend from the current generator and are placed in communication with the skin of the patient. The current then passes through the nerve fibers and the response is measured as discussed above.

Various experimental protocols can be run using this type of device. For example, using one technique, current is repeatedly applied and the evoked action potentials measured. By repeating the procedure the signal is separated from the noise. Thus, by measuring the distance between the stimulating and recording electrodes, and by knowing the time delay between electrical stimulation and recording, it is possible to calculate conduction velocity.

The mechanical drive used in the various mechanical testing apparatus may comprise a model GWV4 manufactured by Gearing and Watson. This driver has a frequency range of 0–12 kHz and a maximum displacement of ±2.5 mm. During operation, the driver's motion is controlled by the digital to analog output from the computer. In one embodiment of the system, the software is programmed to generate the stimuli set forth in Table I below

TABLE I

STIMULATION PARAMATERS TABLE

| Stimulus | Freq. | Amp. range | Duration (sec.) | Indentation (velocity) |
|---|---|---|---|---|
| Vib. 10 Hz | 10 Hz | 0–400 μm | 0.5 | n/a |
| Vib. 50 Hz | 50 Hz | 0–400 μm | 0.5 | n/a |
| Vib. 150 Hz | 150 Hz | 0–304 μm | 0.5 | n/a |
| Vib. 250 Hz | 250 Hz | 0–165 μm | 0.5 | n/a |
| Vib. 500 Hz | 500 Hz | 0–39.2 μm | 0.5 | n/a |
| variable | n/a | 0–400 μm | 0.5 | 10 μm/msec |

Additional apparatus may be utilized in order to obtain the data desired. For example, for some procedures it may be desirable to place the pressure cuff 38 (corresponding to cuff 138 in FIG. 2) around the arm of the patient while the test is taking place in order to provoke a condition such as carpal tunnel syndrome. As mentioned, above, the pressure cuff is controlled by the control systems of the apparatus by way of control module 18.

In some cases it may also be desirable to place earphones on the patient so that he does not receive any auditory clues as to the operation of the testing apparatus. This technique helps to remove some of the possibility of error through the patient hearing and anticipating the stimulus.

In summary, the present invention provides multiple testing apparatus for administering cutaneous stimulation to a patient in a controlled and reproducible manner. The present invention provides the capability of testing for multiple types of disorders and testings multiple types of nerve fibers and sensory mechanisms.

3. Testing Module

Figure 3:
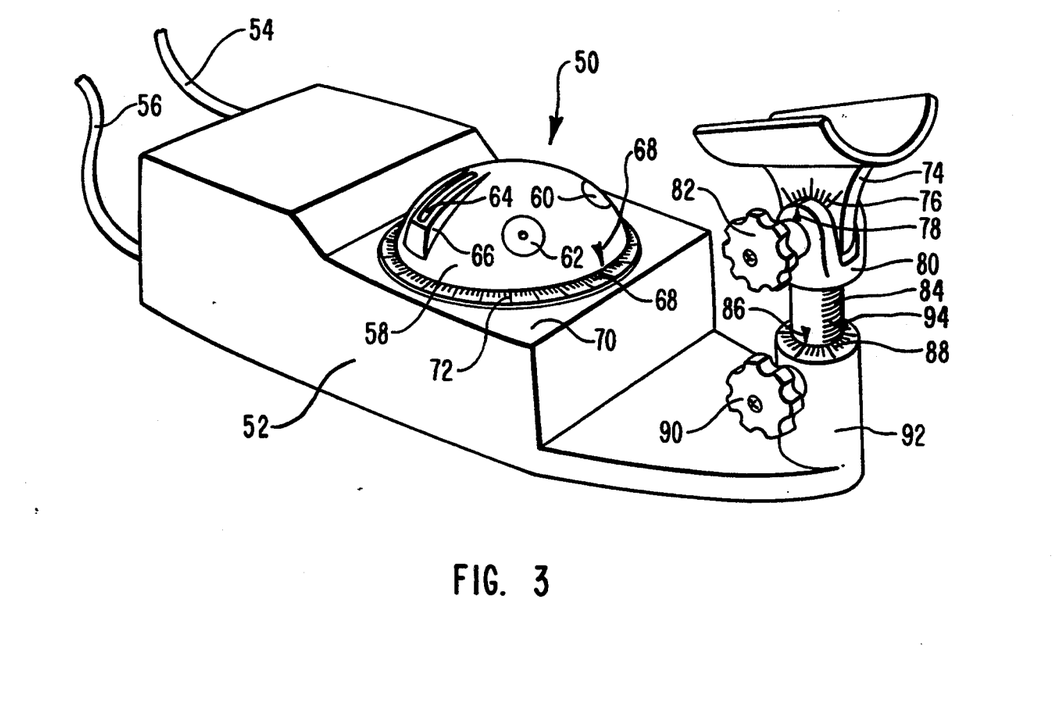
FIG. 3 is a perspective view of one embodiment of a testing module which forms a part of the apparatus of the present invention.
Figure 4:
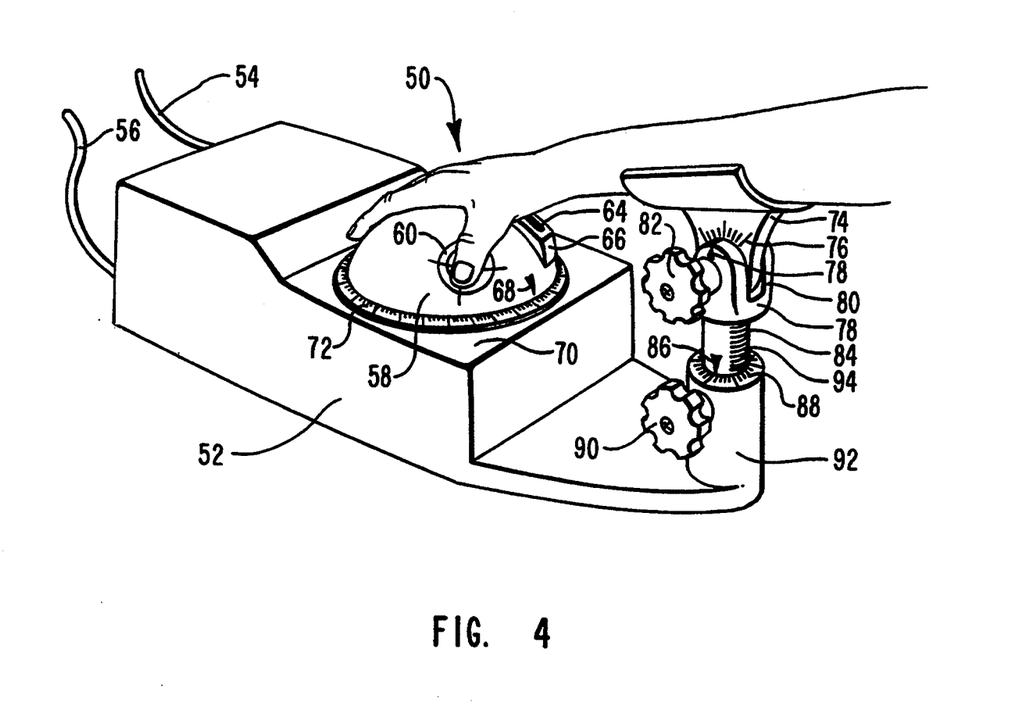
FIG. 4 is a perspective view of the testing module of FIG. 3 in use by a patient.

The present invention provides a unique testing module for use in connection with the device. The testing module is illustrated in FIGS. 3 and 4 where it is generally designated 50. The testing module is comprised of a housing 52 which is manufactured in the desired configuration and size. The housing 52 may be made of any acceptable material, including various types of plastic and fiberglass materials.

Contained within the interior of the housing 52 is one or more of the testing apparatus described above. The necessary mechanisms for performing various cutaneous tests can be positioned within the housing, including mechanisms for touch, vibrotaction, pin pricks, temperature, current, and two point discrimination testing.

These apparatus are placed in communication with the necessary power and control elements, including specifically computer 10, by means of conventional wiring. The wiring is represented in the drawings by cables 54 and 56. As can be seen in FIG. 2, the cables 54 and 56 attach the testing module 50 to the control module 18, and thereby placing the testing module 50 in communication with the computer 10.

The testing module 50 is also equipped with a unique hemispherical dome structure 58. The dome 58 is configured such that the portion of the patient's anatomy to be tested can rest comfortably over the dome. In FIG. 4, for example, the testing module 50 is illustrated with a human hand positioned over the dome.

It is found that the shape of the dome is particularly adaptable to use in the present apparatus. Referring to FIG. 3, it will be appreciated that the dome 58 is ergonomically designed such that a probe from a testing apparatus protrudes through the dome in such a manner that the fingers of the patient can be contacted. As mentioned above, the rounded surface conforms to the general resting position of the hand, such that the hand can rest on the dome without stress during the testing procedures.

As illustrated in FIG. 3, the dome will have one or more openings disposed through its surface. The openings shown in FIG. 3 are designated 60, 62, and 64. Openings 60 and 62 are generally circular and relatively small. As will be discussed in further detail below, these openings are configured such that a single probe can be made to protrude from the openings. It is anticipated that probes for conducting touch, vibrotaction, pin prick, constant current, and temperature tests will be capable of easily extending through openings 60 and 62 and contacting the skin of the patient.

Opening 64 has a somewhat different configuration. Opening 64 comprises an elongated slot. The opening 64 may also include associated ridges 66 such that the slope of the dome 58 is modified slightly in the vicinity of opening 64. Opening 64 is particularly designed to receive the two point discrimination mechanism discussed above. By providing a slot it is possible for two or more probes to be spaced apart for impact on the patient's skin.

As can be appreciated with reference to FIG. 3, the dome 58 and the testing module 50 are provided with corresponding indicia. The dome 58 includes an arrow 68 which points toward the base 70 of the module. The module, in turn, is provided with a plurality of markings 72 around the base of the dome 58. Using the arrow 68 and the corresponding markings 72 on the module it is possible to accurately position the dome 58. Since, as will be discussed in greater detail below, the dome 58 is rotatable, providing the capability of accurately positioning the dome 58 with respect to the remainder of the device is important in obtaining accurate and reproducible data. It should be appreciated that in other embodiments the indicia can be supplemented with potentiometers and other devices such that the position of the dome is sensed and the position transmitted to the computer. Thus, this information can be stored by the computer such that subsequent tests can be performed in relation to the position of the dome in previous tests. In a further embodiment, the dome may be motorized such that the computer can automatically position the dome at a precise location.

As illustrated in FIGS. 3 and 4, the testing module is also provided with an arm rest 74. The arm rest 74 provides important capabilities in performing certain types of tests. For example, if the testing protocol is extensive, the patient may tire during the testing unless provided with means to support the patient's arm. Thus, the arm rest allows the patient to maintain a relatively relaxed posture during the testing procedure.

In addition, in certain tests it may be important to aggravate the suspected condition in order to perform early detection tests for a particular condition. For example, in the case of carpal tunnel screening it has been reported that provocative testing by means of wrist flexion provides increased ability to detect the onset of carpal tunnel syndrome. Thus, it is advantageous to have the capability of positioning the wrist such that it is flexed sufficiently to provide for more accurate detection of carpal tunnel syndrome.

In order to reproducibility position the wrist, the arm rest 74 is simply placed in the desired position. Then the patient rests his forearm on the arm rest, and places his hand on the dome 58. This then provides the means for conveniently placing the patient in a particular desired position. Once this is accomplished, accurate and reproducible carpal tunnel screening can be performed.

It will be appreciated from FIGS. 3 and 4 that the arm rest 74 apparatus is also provided with three series of indicia. These indicia allow the user of the device to accurately position the arm rest with respect to the remainder of the testing module.

In particular, the arm rest 74 is provided with a first set of indicia 76. These indicia correspond to an arrow 78, or other mark or markings, on the arm rest support bracket 80. The arm rest 74 is positioned by loosening knob 82, which is attached to a corresponding bolt (not shown) which protrudes through the arm rest 74 and the support bracket 80. The indicia 76 and the arrow 78 are aligned and the bracket 80 and arm rest 74 are secured in position by tightening the knob 82. This mechanism provides a simple and reliable mechanism for adjusting the arm rest 74 in a generally vertical rotational plane.

A similar mechanism is provided for adjusting the arm rest 74 within a generally horizontal rotational plane. The arm rest riser 84 is provide with an arrow 86, or other mark or markings. The arrow 86 in turn corresponds to a plurality of indicia 88 contained on the test module 50. In order to adjust the arm rest, it is simply necessary to loosen knob 90 and its associated bolt (not shown), position the arm rest 74 using the arrow 86 and the indica 88, and then tighten the knob 90 and bolt.

The arm rest 74 is also provided with a height adjustment. The arm rest riser 84 protrudes into the receiving socket 92 of the testing module 50. The height of the arm rest 74 is indicated by indicia 94 located on the riser. Thus, when knob 90 is loosened, the riser can be raised or lowered until a selected mark corresponds to the top of the arm rest socket 92. At this time, the knob 90 is tightened such that the arm rest 74 remains securely in place.

The manner of operation of the testing module 50 can be more fully appreciated by reference to FIG. 4. In order to perform a testing procedure, the arm rest 74 is adjusted as desired. As mentioned above, in a typical test, the arm rest 74 is positioned such that it comfortably supports the forearm of the patient. In certain types of provocative tests, however, the arm rest 74 may be positioned such that the wrist is flexed or such that other desired positions are achieved.

As was discussed above, it is possible to adjust the arm rest 74 in a vertical rotational plane. It is also possible to adjust the arm rest in a horizontal rotational plane. The arm rest 74 can also be easily raised or lowered as desired. Thus, accurate selective positioning of the arm rest 74 is provided.

Once the arm rest is positioned, the dome 58 is rotated such that the desired testing apparatus will protrude through the desired opening and impacted the selected portion of the patient's anatomy. In FIG. 4 it can be seen that the patient's thumb is placed over opening 60 such that a particular testing apparatus impacts the patient's thumb. At the same time, the remainder of the patient's hand rests comfortably over the dome 58.

Once in position, the operator types in the required code to initiate the test sequence. Using the programming code described herein, it is not necessary for the operator to make further entries during the test. Rather, the computer controls the administration of a series of tests using the testing apparatus in contact with the patient's thumb. Once this set of tests is concluded, the dome 58 may be rotated and further tests accomplished.

Figure 5:
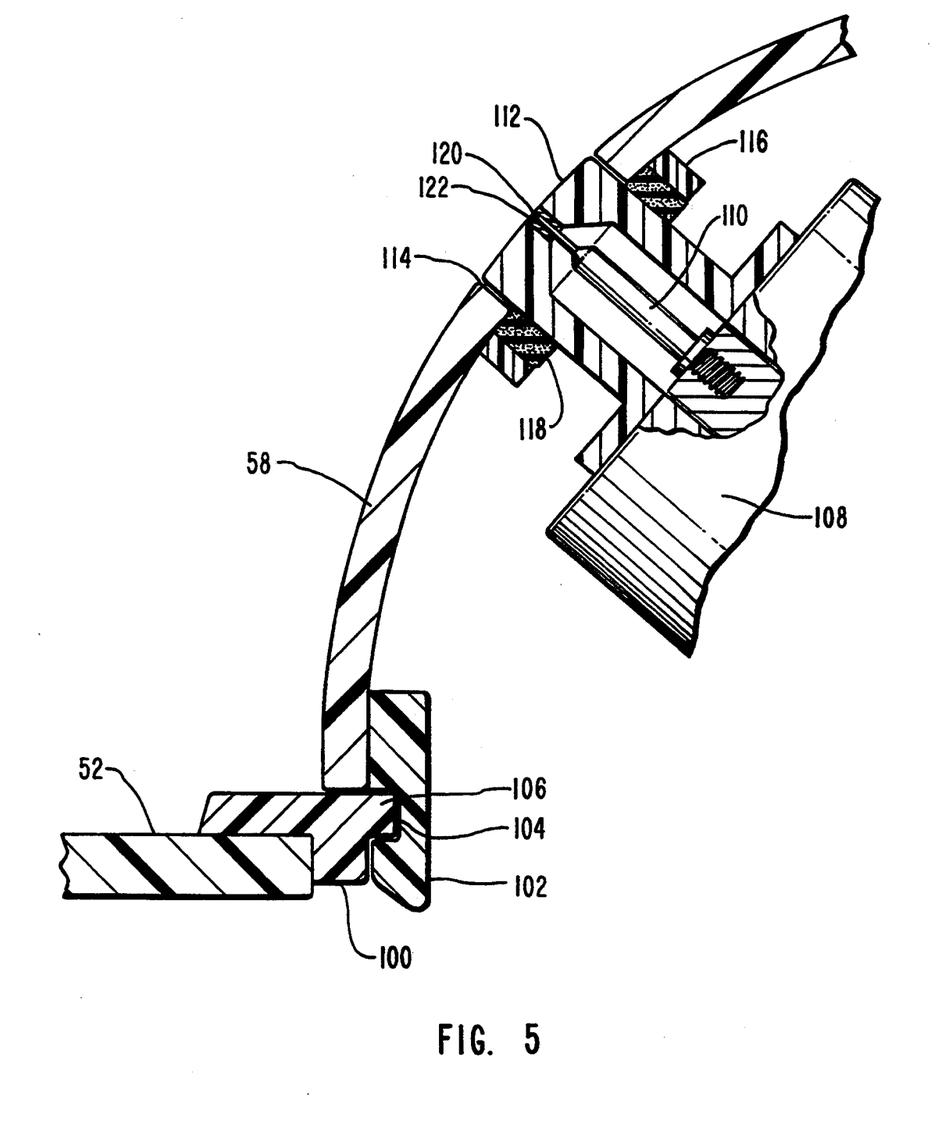
FIG. 5 is a cross sectional view of the dome and related structures of the testing module.

The operation of the dome can be more fully appreciated with reference to FIG. 5. A portion of the dome 58 is shown in cross section, as is a portion of the base of the testing module housing 52. The dome 58 and corresponding portions of the housing 52 are constructed such that the dome 58 can be easily rotated. The dome 58 is preferably constructed of polyester resin reinforced with three layers of fiberglass cloth, for a total thickness of 0.084 inches. The housing 52 is constructed of ¼ inch acrylic plastic glued with Weldon 3 solvent cement. The dome 58 and the housing 52 are coated with two layers of epoxy primer and two layers of epoxy paint. Any substantially rigid and durable material of low thermal conductivity may be selected.

Attached to the housing 52 is a substantially circular ring 100 of Delrin ® material. Delrin ® comprises acetyl resin and is available commercially from DuPont. Delrin ® is selected because it provides a very low friction surface, and when placed in contact with another Delrin ® surface, the surfaces readily slide over one another. It will be appreciated that other similar materials could also be selected.

A second ring 102 of Delrin ® material is securely attached to the interior of the dome 58. The second ring 102 is provided with a groove 104 which is configured such that it receives a tongue 106 of ring 100. In this manner, the dome 58 is held in place with respect to the testing module 50, and is at the same time easily rotated with respect to the housing 52 in that the Delrin ® rings 100 and 102 readily slide over one another.

Also illustrated in FIG. 5 is a testing apparatus 108. Testing apparatus 108 comprises means for administering touch, vibrotaction, pin prick, temperature, or two point discrimination tests. Other similar types of testing apparatus may also be substituted. As mentioned above, the testing apparatus described in U.S. Pat. No. 5,022,407 and similar types of known testing apparatus can be configured such that they readily reside within dome 58.

Extending out of the testing apparatus 108 is a probe 110. The probe 110 is positioned such that during the testing procedure, the probe 110 will protrude above the surface of the dome 58 and impact the patient. As can be seen from FIG. 5, the probe 110 is surrounded by a probe housing 112 which fits within opening 114 (which may, for example correspond to openings 60 and 62 in FIG. 3). The probe housing 112 is also preferably constructed of Delrin material so that it can be rotated within the opening 114.

A small ring of Delrin ® material 116, along with an associated ring of insulation 118 may be attached to the interior of the dome and circumscribe a portion of the testing apparatus. In this manner, the testing apparatus is secured in place with respect to the dome 58 and the opening 114, even when the dome is rotated.

In order to provide direct information to the computer concerning the location of the probe 110 with respect to the dome 58, it is desirable to provide means for confirming the location of the probe. One such preferred means comprises placing a small infrared light 120 on the probe and a silicon position sensor strip 122 on the probe housing 112 next to the probe. The position sensor provides means for monitoring the position of the light beam. In one preferred embodiment, the output voltage from one edge of the sensor is compared to the voltage at the other edge and the difference between the two sensor outputs is proportional to the light beam position. The sum of the outputs from the two sensor outputs is compared to a reference voltage and the LED light intensity is them maintained through feedback at a constant level and this corrects for factors such as aging, dust accumulation, and misalignments between the LED and the sensor that might occur over time.

The LED strip is placed in electrical communication with the computer. In a presently preferred embodiment, there is a feedback control electronic circuit that forces the probe to follow the command signal from the computer. An advantage of electronic feedback is that it forces the probe to move in the required manner independent of the compliance and pressure exerted by the patient's cutaneous surface. It is preferred to use a parallel expansion board 16 with a 12-bit analog-to-digital converter and use the computer to automatically track the location of the probe. Thus, it is possible to automatically calibrate the testing apparatus and to receive direct information in that event of malfunction of the device. One acceptable LED light is model MLE071 manufactured by Motorola, while an acceptable silicon position sensor is a position sensitive detector, model S3931-01 available from Hammamatsu Corporation.

4. Computer System

Referring once again to FIGS. 1 and 2, the apparatus for testing cutaneous response is provided with a computer 10 capable of providing various control functions, administering stimulus of selected amplitude and time course, and of recording data. In some testing sequences, the computer, through the associated software, will generate subsequent stimuli based upon the responses received when earlier stimuli are administered.

The computer is preferably equivalent to an International Business Machines (IBM) microcomputer having a 486 Intel chip with a relatively large hard disk (60–120

MB), in an SX configuration, operating in the 25–40 mHz range. The monitor 12 will preferably comprise a super VGA graphics color monitor. The computer may be connected to a standard printer so that data and medical report forms can be printed directly from the cutaneous testing apparatus. A laser or ink jet computer is preferred because they are quiet and will not disturb ongoing patient testing. The computer contains diskette and cassette systems for backup of patient data on two types of storage media. Also accompanying the microcomputer 10 is a standard keyboard 14. These items are commercially available in the art and are readily available from numerous commercial sources.

As mentioned above, the computer may also be equipped with a 12-bit D-A and A-D converter. One example is DAS-16 board from Keithley Metrabyte, Inc. which runs at 50 kHz. With this board is provided the capability of providing higher frequency sine waves up to 500 Hz, possibly going up to 800 Hz. This may be important because there is some literature that suggests that Pacinian corpuscles are able to respond to frequencies up to 800 Hz.

As illustrated in FIG. 1, the computer 10 has an associated parallel expansion board 16. The parallel expansion board is commercially available and may comprise a board manufactured by the Qua Tech Company of Akron, Ohio, which is referred as model PXB721, accompanied by a digital to analog converter module referred to as model DM8-10.

It will be appreciated that the computer 10 and the control module 18 may be placed in communication by other methods known in the computer art. For example, the computer 10 and the control module 18 may be placed in communication by way of an RS232 port in such a manner that the data acquisition card need not be placed within the computer. Rather, the board or its equivalent may be placed with the control module 18, and control module 18 may then be connected directly into a standard port in the back of the computer. Thus, an operator who is not particularly familiar with computer hardware is capable of easily connecting the necessary components. In addition, using this type of mechanism avoids possible damage to the various electrical components of the computer and the board.

In the illustrated system the control module 18 preferably comprises a power supply, a printed circuit board containing a 2.5 KHz clock, logic circuits, buffer amplifiers, and feedback controlled power amplifiers for the testing apparatus.

Thus, it will be appreciated that the present invention provides a high degree of computer control. The apparatus also provides computer means for recording data and for generating testing sequences in response to the data recorded. This is all accomplished by the use of commercially available computer hardware.

5. Testing Procedures and Computer Software

Using any of the mechanisms discussed above, it is possible to automatically cycle through a "threshold" procedure or any other predetermined set of stimuli. In the "threshold" procedure the computer administers repeated stimuli until the patient indicates that a particular stimulus is felt. In one preferred embodiment of the threshold procedure, the amplitude of the stimulus is initiated at or near the limit of the "normal" threshold and then performs first a "search" and then a "staircase" routine. During the search, the computer increases or decreases the stimulus by a relatively large increment and over a large enough number of cycles that the threshold will be converged near the patient's threshold whether it be low or high. For example, the increment may be set to 25% and the number of cycles to seven (7) steps. The computer then begins the "staircase" routine in which the incremental change in stimulus amplitude is significantly smaller, such as 10%. The computer then cycles the stimulus amplitude down until the stimulus is no longer felt and up until the stimulus is perceived. Threshold is defined as the average difference between maximum and minimum amplitudes over a standard number of cycles, which may, for example, be two.

As mentioned above, the patient simply depresses and then releases the button 135, moves a slider, or responds in some other way, when the stimulus is first felt. In some embodiments of the invention, the response to the stimulus may be measured directly by a monitor 136 which senses electrical or physiological changes. In that regard, the programming code may be designed in such a manner that the decision time is set at a specific length. If the patient depresses the button after the decisions time, then an identical stimulus is repeated. Thus, the patient will not be able to disable the testing sequence by pressing the button over a long period of time. In the present embodiment, the computer code is designed so that the time between stimuli is randomized, thus preventing the patient from guessing the timing of the stimulus presentation. Hence, the software is designed such that a patient with an abnormally high sensory threshold will be unable to lower of his threshold reading into the normal range. It is also important to minimize the chance that patient's with normal thresholds can simulate an elevated sensory threshold. In this case, the computer repeats that stimulus routine at extremely high and low values. In an authentic patient it will converge on the same value of sensory threshold independent of the beginning stimulus; whereas it is extremely difficult for the malingering patient to converge repeatedly to the same stimulus value because it is difficult to estimate the absolute amplitude. The software may, for example, run two or more search routines simultaneously.

The present invention automatically deals with many record keeping tasks which would otherwise be burdensome to the technician. Moreover, the present system's organization of the data recorded during a test allows the data to be manipulated in many desirable ways which would be impractical if the data were manually recorded.

For example, the system described herein can keep a permanent record of the data from multiple testing sessions for each patient and can provide graphical and tabular summaries of the performance of a given patient over time providing an objective measure of the patient's progress. It is possible to compare the data obtained with baseline data loaded onto the computer. Thus, the present invention provides for significant improvements in the ability of medical professionals to diagnose somatic neuropathy and monitor somatosensory neural function.

Using the present invention, it is possible to screen workers and the work place for ergonomic factors. Workers may be tested in order to establish baseline data. Changes in the work place can then be made and the patient's re-tested to determine whether the changes resulted in better worker performance. In this manner it is possible to design the work place in such a manner that ergonomic issues are dealt with efficiently. For example, it is possible to screen the work place for its tendency to induce carpal tunnel syndrome in workers.

As mentioned above, it is also possible to provide the computer with certain baseline data against which the patient's response is compared. For example, normal data can be accumulated, as can representative data for various conditions that might influence sensory threshold in general, or might prejudice a patient toward compression injury. Such conditions may including, for example, carpal tunnel syndrome, old age, leprosy, nerve regeneration, artificial and replacement skin (such as that used in treating burn victims), and numerous other disease or abnormal conditions. Once the desired data is loaded onto the computer 10, it is possible to compare the data obtained by measuring the patient response with either a normal baseline, or a baseline which is representative of particular disease, injury, or degenerative conditions.

The baseline data can easily be updated as needed and loaded onto the computer from a disk or other computer input mechanism. For example, in a commercial embodiment, it may be desirable for the user to subscribe to regular updates of the baseline data. Accordingly, the accuracy and reliability of diagnosis is significantly enhanced by comparing patient response against constantly updated baseline data.

The operation of the system is generally carried out under the direction of programming code run on the microcomputer 10. Among the functions carried out during the operation of the system using the code hereto are:

1) Creation of new patient files;
2) Patient log in and log out;
3) Testing of touch threshold to indentation stimuli using a staircase procedure;
4) Testing of touch threshold to sinusoidal stimuli using a staircase procedure;
5) Testing of two point discrimination response using a staircase procedure;
6) Testing of temperature threshold using a staircase procedure;
7) Testing of pain threshold using a pinprick and staircase procedure;
8) Magnitude scaling with skin indentations;
9) Magnitude scaling with sinusoidal skin indentations;
10) Magnitude scaling of two-point separation;
11) Magnitude scaling of temperature;
12) Magnitude scaling of pain;
13) Constant current application;
14) Display of patient data for a given type of test over time in both tabular and graphical forms; and
15) Printing out tabular or graphical displays of patient performance:
16) Comparing data obtained with baseline measurements.

The software also controls the precise movement of the probe as it indents the skin. The software also performs calibration checks on the probe movement. In the attached example of programming code, the code is written in C language and is designed in modular form with separate section for LOG IN, search and retrieval, stimulation, report generation, and personal history. The code may also be designed to provide automatic calibration checks at various stages in the operation of the device.

Furthermore, using the code, when a patient is tested for the first time, the technician creates a data file in which is stored the patient's name and an identification number. Each time a test is run on the patient, a record of the date, the test parameters and the patient's responses are appended to the file. Subsequently, the user may extract data from this file for analysis and graphical display or tabular summary. This information may be sent either to the display or to a printer (not shown) for a permanent written report on the patient's performance. This file is stored in ASCII format, so it may be reviewed, edited, or printed with any number of commercially available word processing programs. Using the code, the technician is also able to preprogram a sequence of tests, and execute this sequence automatically by calling up a file with the sequence and parameter information stored in it.

In one embodiment of the programming code, at the beginning of each test sequence the technician is presented with a menu from which the operation to be performed is selected. The parameters for each test are provided with default values, which the technician may accept or change as desired. The operator instructs the patient on the basic procedure to be followed, and initiates the test. Responses of the subject or patient are typed into the microcomputer 10 by the operator, as prompted on the display. Inappropriate entries are trapped, and the technician is requested to provide a valid response.

Other functions and data may be added to the code as desired. For example, application of constant current stimuli can also be controlled in a similar manner. Comparing baseline date with data collected during test runs can also be completed by appropriate modification to the programming code and the input of appropriate data into computer 10.

6. Summary

In summary, the present invention provides means for accurately and reproducibility administering cutaneous stimulation in order to test for various types of diseases and degenerative conditions. The present invention also provides apparatus and method for automatically testing a patient's response to various modes of cutaneous stimulation which does not require special expertise to operate and maintains a record of the results of the testing. The device imposes quantifiably accurate stimuli upon command and carries out the testing in a relatively short period of time.

The device represents an advancement in the art in that it is able to control the amplitude, velocity, and time course of stimulation. The device also measures human cutaneous sensory threshold in a quick and efficient manner, thus being capable of rapidly screening subjects for early signs of sensory deficit. As discussed above, the system may be operated in such a manner that neither the operator nor the subject is aware of the timing of the stimulus delivery. The device also provides computer means for receiving data and for controlling the set of stimuli administered in order to obtain a predetermined data set.

The present invention may be embodied in other specific forms without departing from its spirit or essential characteristics. The described embodiment is to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A testing module comprising:
   a patient cutaneous testing apparatus for performing a cutaneous test;
   a hemispherical dome having an exterior and an interior, said dome configured such that said testing apparatus can substantially reside within the interior of said dome and such that a part of a patient's anatomy to be tested can rest over the exterior of the dome during a cutaneous testing procedure, allowing the patient to maintain a relatively relaxed posture during the testing procedure; and
   means for rotating said dome,
   wherein said testing apparatus is positioned during operation to administer a predetermined patient stimulus at or beyond the exterior of said dome, and wherein said testing apparatus is capable of being accurately and reproducibly positioned with respect to the part of the patient's anatomy to be tested.

2. A testing module as defined in claim 1 further comprising an opening disposed through said dome and positioned such that said testing apparatus can partially protrude through said dome and contact the skin of said patient.

3. A testing module as defined in claim 1 further comprising means for defining the position of the dome relative to the remainder of the module.

4. A testing module as defined in claim 3 wherein said means for defining the position of the dome relative to the remainder of the module comprises indicia on said dome and further indicia on another portion of said module.

5. A testing module as defined in claim 1 wherein said dome is configured such that a patient's hand can rest over the exterior of the dome during a cutaneous testing procedure on the hand or the digits.

6. A testing module as defined in claim 1 wherein said module further comprises an arm rest positioned near said dome such that when a portion of the patient's hand rests over said exterior of said dome during the testing procedure, the patient's arm may rest on said arm rest.

7. A testing module as defined in claim 6 further comprising means for defining the position of the arm rest relative to the remainder of the module.

8. A testing module as defined in claim 7 wherein said means for defining the position of the arm rest relative to the remainder of the module comprise indicia on said arm rest and further indicia on a further portion of said module.

9. A testing module as defined in claim 8 comprising multiple sets of indicia on said arm rest and on further portions of said module.

10. A testing module as defined in claim 9 wherein said indicia define the position of the arm rest within a vertical rotational plane.

11. A testing module as defined in claim 9 wherein said indicia define the position of the arm rest within a horizontal rotational plane.

12. A testing module as defined in claim 1 wherein said testing apparatus comprises temperature means for applying a nonambient temperature to the patient's skin.

13. A testing module as defined in claim 1 wherein said testing apparatus comprises pinprick means for pricking the patient's skin.

14. A testing module as defined in claim 1 wherein said testing apparatus comprises means for indenting the patient's skin.

15. A testing module as defined in claim 1 wherein said testing apparatus comprises means for vibrating the patient's skin.

16. A testing module as defined in claim 1 wherein said testing apparatus comprises means for making two spaced apart contacts with the patient's skin.

17. A testing module comprising:
    a patient cutaneous testing apparatus including a probe for performing a cutaneous test;
    a hemispherical dome having an interior and an exterior, said testing apparatus being capable of substantially residing within said interior of said dome, said dome configured such that a part of a patient's anatomy to be tested can rest over the exterior of the dome during a cutaneous testing procedure;
    means for accurately and reproducibly positioning the part of the patient's anatomy to be tested with respect to said probe, said means comprising rotation means for rotating said dome and positioning means for accurately positioning said dome during operation of said rotation means,
    wherein said probe is positioned such that when in operation it administers a predetermined patient stimulus at or beyond the exterior of said dome.

18. A testing module as defined in claim 17, further comprising a housing, wherein said dome is rotatable with respect to said housing, and wherein said rotation means comprises:
    a first substantially circular ring attached to said housing, having a tongue, and having a very low friction surface; and
    a second substantially circular ring securely attached to said dome and having a groove which is configured to receive said tongue of said first substantially circular ring.

19. A testing module as defined in claim 17, further comprising a base supporting said dome, wherein said positioning means for accurately positioning said dome during operation of said rotation means comprises indicia located on said base and said dome.

20. A testing module as defined in claim 17, wherein said positioning means for accurately positioning said dome during operation of said rotation means comprises a potentiometer for sensing the position of said dome.

21. A testing module as defined in claim 17, wherein said means for accurately and reproducibly positioning the part of the patient's anatomy to be tested with respect to said probe comprises an arm rest positioned near said dome such that when a portion of the patient's hand rests over said exterior of said dome during the testing procedure, the patient's arm may rest on said arm rest.

22. A testing module as defined in claim 21, wherein said arm rest comprises a first mechanism for adjusting said arm rest in a generally vertical rotational plane, a second mechanism for adjusting said arm rest in a generally horizontal rotational plane, and a height adjustment mechanism.

* * * * *